United States Patent
Fulcher et al.

(10) Patent No.: US 10,266,287 B2
(45) Date of Patent: Apr. 23, 2019

(54) METHOD OF MANUFACTURE OF A DISPENSER

(71) Applicant: ESSENTRA FILTER PRODUCTS DEVELOPMENT CO. PTE. LTD, Singapore (SG)

(72) Inventors: Gary Fulcher, Newcastle (GB); James Reed, Newcastle (GB)

(73) Assignee: ESSENTRA FILTER PRODUCTS DEVELOPMENT CO. PTE. LTD, Singapore (SG)

( * ) Notice: Subject to any disclaimer, the term of this patent is extended or adjusted under 35 U.S.C. 154(b) by 456 days.

(21) Appl. No.: 14/895,311

(22) PCT Filed: Jun. 2, 2014

(86) PCT No.: PCT/EP2014/061320
§ 371 (c)(1),
(2) Date: Dec. 2, 2015

(87) PCT Pub. No.: WO2014/195250
PCT Pub. Date: Dec. 14, 2014

(65) Prior Publication Data
US 2016/0122047 A1   May 5, 2016

(30) Foreign Application Priority Data

Jun. 3, 2013 (GB) .................................. 1309923.9
Jul. 24, 2013 (GB) .................................. 1313251.9
Apr. 30, 2014 (GB) .................................. 1407620.2

(51) Int. Cl.
B65B 9/06    (2012.01)
A24B 13/00   (2006.01)
(Continued)

(52) U.S. Cl.
CPC ............... *B65B 9/06* (2013.01); *A24B 13/00* (2013.01); *A24F 23/02* (2013.01); *A61J 3/02* (2013.01);
(Continued)

(58) Field of Classification Search
USPC .............................. 53/412, 451; 128/203.15
See application file for complete search history.

(56) References Cited

U.S. PATENT DOCUMENTS 3,550,508 A * 12/1970 Sprinkle ............... A24D 3/0216
                                                         131/337
3,762,281 A * 10/1973 Burrus ................. A24D 3/0225
                                                          493/47
(Continued)

FOREIGN PATENT DOCUMENTS

DE    1 243 072       6/1967
EP    0 150 810 A3    8/1985
(Continued)

OTHER PUBLICATIONS

Notification of Transmittal of International Search Report issued in Application No. PCT/EP2014/061320 dated Jul. 14, 2014 (1 page).
(Continued)

*Primary Examiner* — Michelle Lopez
*Assistant Examiner* — Chinyere J Rushing-Tucker
(74) *Attorney, Agent, or Firm* — Flynn Thiel, P.C.

(57) ABSTRACT

Processes for the manufacture of dispensers for an agent, for example, a therapeutic agent, for example a particulate therapeutic agent or a particulate foodstuff or snuff. The processes comprise the steps of continuously advancing, longitudinally, a flow of longitudinally extending dispensers and wrapping these dispensers by a common product wrapper. The dispensers comprise at least a base element (72), a
(Continued)

cylindrical tubular element (73) with a cavity (74), a capping element (76) and a common outer wrapper (77).

9 Claims, 5 Drawing Sheets

(51) Int. Cl.
| | | |
|---|---|---|
| *B65B 9/067* | (2012.01) | |
| *B65B 9/073* | (2012.01) | |
| *A24F 23/02* | (2006.01) | |
| *A61J 3/02* | (2006.01) | |
| *B65B 61/06* | (2006.01) | |
| *B65B 61/18* | (2006.01) | |
| *A24D 3/04* | (2006.01) | |
| *A61M 15/06* | (2006.01) | |

(52) U.S. Cl.
CPC .............. *B65B 9/067* (2013.01); *B65B 9/073* (2013.01); *B65B 61/06* (2013.01); *B65B 61/18* (2013.01); *A24D 3/048* (2013.01); *A61M 15/06* (2013.01)

(56) References Cited

U.S. PATENT DOCUMENTS

| | | | | |
|---|---|---|---|---|
| 3,807,286 A * | 4/1974 | Sexstone | ............. | A24D 3/0225 493/45 |
| 4,972,855 A * | 11/1990 | Kuriyama | ............. | A24B 15/14 131/111 |
| 4,991,606 A * | 2/1991 | Serrano | ................ | A24B 15/165 131/194 |
| 5,331,981 A * | 7/1994 | Tamaoki | ................ | A24B 15/00 131/335 |
| 5,613,504 A * | 3/1997 | Collins | ................ | A24F 47/008 131/194 |
| 5,687,746 A * | 11/1997 | Rose | ..................... | A24F 47/002 128/202.21 |
| 5,746,227 A | 5/1998 | Rose et al. | | |
| 5,780,058 A | 7/1998 | Wong et al. | | |
| 5,992,631 A | 11/1999 | Eeckhout et al. | | |
| 6,082,368 A * | 7/2000 | Brown | ..................... | A23G 3/36 131/270 |
| 6,336,896 B1 * | 1/2002 | Hsu | ..................... | A24C 5/475 493/39 |
| 2005/0106188 A1 | 5/2005 | Sedaghat Kerdar et al. | | |
| 2008/0216847 A1 * | 9/2008 | Demmer | .................. | A24C 5/40 131/70 |
| 2011/0247637 A1 * | 10/2011 | Duke | ..................... | A24D 3/048 131/108 |
| 2014/0046273 A1 * | 2/2014 | Kang | .................. | A61M 35/003 53/467 |
| 2015/0104516 A1 * | 4/2015 | Cafiero | ..................... | A61J 3/02 424/489 |
| 2015/0208720 A1 * | 7/2015 | Kadiric | .................. | A24C 5/476 131/281 |

FOREIGN PATENT DOCUMENTS

| | | |
|---|---|---|
| EP | 1 072 201 A2 | 1/2001 |
| EP | 1 164 879 A1 | 1/2002 |
| EP | 2 062 484 A1 | 5/2009 |
| GB | 873982 | 8/1961 |
| GB | 2 118 423 A | 11/1983 |
| GB | 2 303 114 A | 2/1997 |
| WO | WO 96/39880 A1 | 12/1996 |
| WO | WO 02/038208 A3 | 5/2002 |
| WO | WO 2005/049449 A1 | 6/2005 |
| WO | WO 2006/067627 A1 | 6/2006 |
| WO | WO 2007/135414 A1 | 11/2007 |
| WO | WO 2011/114946 A1 | 9/2011 |
| WO | WO 2013/174975 A1 | 11/2013 |
| WO | WO 2014/023555 A1 | 2/2014 |

OTHER PUBLICATIONS

International Search Report issued in Application No. PCT/EP2014/061320 dated Jul. 14, 2014 (8 pages).
Written Opinion of the International Searching Authority issued in Application No. PCT/EP2014/061320 dated Jul. 14, 2014 (3 pages).
Search Report of Great Britain Patent Office issued in Application No. GB1309923.9 dated Oct. 17, 2013 (5 pages).
Search Report of Great Britain Patent Office issued in Application No. GB1407620.2 dated Aug. 26, 2014 (5 pages).

* cited by examiner

METHOD OF MANUFACTURE OF A DISPENSER

The present invention relates to methods of manufacture of dispensers for agents, for example dispensers for particulate materials such as therapeutic agents, snuff, foodstuffs etc.

Therapeutic agents (e.g. pharmaceutically active agents, health supplements and the like) are well known, and may be formulated in various forms depending on the method of administration. For oral administration (which may include sublingual administration) the therapeutic agent may be formulated as a particulate material (e.g. as granules, particles, powder, minicapsules etc.). A dose or doses of particulate material may be held in a sachet or similar container, prior to administration by e.g. tipping into the mouth. Examples of pharmaceuticals which are particulate materials (e.g. powders) for oral administration include Gaviscon Instants Oral Powder, marketed by Reckitt Benckiser Healthcare.

Powdered alcohol products are also known. Alcohol can be adsorbed on or in a substrate (e.g. a sugar derivative such as a cyclodextrin), and can then be handled as a particulate material (a powder).

There is a need for a dispenser product for agents, for example therapeutic agents, foodstuffs etc. that is disposable, low cost, and capable of being manufactured on a mass scale. Furthermore, it would be desirable to have a product which is able to deliver a reproducible dose of the agent (e.g. therapeutic agent) to the user. Advantageously, the dispenser would have a suitably tactile feel (e.g. mouth feel) in use.

There is provided a dispenser for an agent (e.g. a particulate material, e.g. a particulate agent, e.g. a therapeutic agent, e.g. a particulate therapeutic agent), the dispenser including a longitudinally extending (e.g. generally cylindrical) body comprising: a longitudinally extending (e.g. generally cylindrical) base element;
a (e.g. generally cylindrical) tubular element which extends longitudinally from the base element such that the inner wall of the tubular element defines (e.g. with the base element) a cavity (or reservoir); and
an agent (e.g. a particulate material, e.g. a particulate agent, e.g. a therapeutic agent, e.g. a particulate therapeutic agent) within the cavity or reservoir;
the dispenser optionally including closure means for the cavity or reservoir.

Herein, the term agent means a substance, and includes substances with a particular or specific activity (e.g. therapeutic activity), and foodstuffs (e.g. confectionary foodstuffs such as sherbet). The agent may be a particulate material (e.g. particulate therapeutic agent, powdered alcohol, confectionar such as sherbet powder). The term therapeutic agent includes pharmaceutically active agents/substances, formulations of pharmaceutically active agents/substances, and health supplements. The term particulate agent means an agent/substance/material in the form of particles, and includes granules, particles, powders, minicapsules etc. The term particulate agent includes partial mixtures of the agent (e.g. therapeutic agent) with other component(s) (e.g. a mixture of the agent with an inert diluent).

The dispenser includes the agent (e.g. a particulate material, e.g. a particulate agent, e.g. a therapeutic agent, e.g. a particulate therapeutic agent) located within the cavity/reservoir. The amount (dose) of agent (e.g. a particulate material, e.g. particulate agent, e.g. therapeutic agent, e.g. particulate therapeutic agent) in the cavity is typically sufficient to give an acceptable delivery in use (when dispensed). The amount of agent in the cavity may be 0.05 to 0.5 $cm^3$, for example 0.10 $cm^3$ to 0.20 $cm^3$. An acceptable delivery amount (volume) for a particulate agent would typically be in the order of up to 0.2 $cm^3$ per dose, for example 0.15 $cm^3$ per dose (These figures would typically apply to a dispenser of around 8 mm diameter delivering a therapeutic agent; for other applications, e.g. foodstuffs, higher delivery volumes may be required and this may be accomplished, for example, by using a higher diameter dispenser, as would be understood by those skilled in the art). Preferably, the cavity includes a single dose, for example 0.10 $cm^3$ to 0.20 $cm^3$, preferably 0.15 $cm^3$ of particulate agent. In other words, a single dose (single use) dispenser is preferred. It is also possible to add a greater amount (volume) of particulate agent to enable more than one dose to be taken from the dispenser, although this is not preferred. The agent (e.g. a particulate material, e.g. a therapeutic agent) is generally and preferably in particulate form (e.g. granules or a powder), but may be another form such a liquid, oil etc.

Preferably, the longitudinally extending body is cylindrical. The external diameter of the body may be from 4 to 15 mm, more preferably 8 to 12 mm. Preferably, the tubular element is cylindrical. The external diameter of the tubular element may be from 4 to 15 mm, more preferably 8 to 12 mm. Preferably, the base element is cylindrical. The external diameter of the base element may be from 4 to 15 mm, more preferably 8 to 12 mm. Preferably, the tubular element and the base have the same, or substantially the same, diameter.

The present invention applies technologies used in the manufacture of cigarette filters and filter elements to produce a dispenser for an agent (e.g. a particulate material, e.g. a particulate agent, e.g. a therapeutic agent, e.g. a particulate therapeutic agent). The product comprises a tubular structure that is closed at one end and has an opening or openings at the other end of the tube. A defined amount or dose of an agent (e.g. a particulate material, e.g. a particulate agent, e.g. a therapeutic agent, e.g. a particulate therapeutic agent) is located within a hollow section (e.g. the cavity) of the tubular structure. A closure means (e.g. a cap or capping member) preferably covers the open end of the dispenser (e.g. tubular element) to ensure that the content (agent) does not inadvertently fall out of the cavity (dispenser) prior to use. The user simply removes this cap before use, inserts the open end of the dispenser (device) into e.g. their mouth, and dispenses the agent (e.g. a particulate material, e.g. a particulate agent, e.g. a therapeutic agent, e.g. a particulate therapeutic agent) by sucking on the dispenser. The applicants have found that the use of materials from the tobacco industry, particularly materials of specific pressure drop, enables the user to readily suck the contents (agent) from the dispenser, thereby enabling a reproducible (and complete) dose of the agent (e.g. therapeutic agent) to be delivered to the user. The materials also have a suitably tactile feel (e.g. mouth feel) in use. The dispenser may be for oral administration of the agent (e.g. a particulate material, e.g. a particulate agent, e.g. particulate foodstuff, e.g. a therapeutic agent, e.g. a particulate therapeutic agent). The dispenser may be for administration of the agent (e.g. a particulate material, e.g. a particulate agent, e.g. a therapeutic agent, e.g. a particulate therapeutic agent) by other routes, e.g. to the nose (by snorting), to the ear etc.

The base element and/or tubular element (of the longitudinally extending body) are preferably porous (although this is not essential). The base element and tubular element may be formed from the same material, or from different materials. The base element and the tubular element may be formed separately, or they may be of unitary construction. If the base element and the tubular element are of unitary construction they may be formed by similar methods to those used to make Filtrona Long Bore SAF filters (see EP1164879). The longitudinally extending body may further comprise a common wrapper, which is engaged around the base element and the tubular element. If the base element and the tubular element are not of unitary construction, for example, the common wrapper may serve to hold the base element and the tubular element in place (e.g. abutted against each other). The base element and/or tubular element may be formed from a bonded fibrous structure, from a folded film, paper or nonwoven material, or formed via an extrusion or moulding process. The base element and/or tubular element may, for example, be made of cellulose acetate, polypropylene, polyester, bicomponent fibre, paper or any other similar material. The base element is preferably porous. The base element is preferably formed of a material which has a low pressure drop, for example a pressure drop of 5 to 350 mm water (for a 10 mm length×8 mm diameter element), for example a pressure drop of 5 to 250 mm water (for a 10 mm length×8 mm diameter element), more preferably a pressure drop of 10 to 300 mm water (for a 10 mm length×8 mm diameter element), for example a pressure drop of 10 to 200 mm water (for a 10 mm length×8 mm diameter element). The use of a porous material having a low pressure drop may facilitate ease of administration of the agent, e.g. by facilitating suction of the agent by the user.

In an example, a dispenser for an agent (e.g. a particulate material, e.g. a particulate agent, e.g. a therapeutic agent, e.g. a particulate therapeutic agent) includes a longitudinally extending (e.g. generally cylindrical) body comprising: a longitudinally extending (e.g. generally cylindrical) base element; and an outer wrapper (e.g. stiff paper wrapper) engaged around the base element; wherein a part of the outer wrapper extends longitudinally beyond a (the upper) face of the base element to form the (e.g. generally cylindrical) tubular element [which extends longitudinally from the base element such that the inner wall of the tubular element defines with the (e.g. upper face of) base element the cavity (or reservoir)]. It will be appreciated that the inner walls of the outer wrapper, together with the face of the base element beyond which they extend, form the cavity (reservoir).

There is provided a dispenser for an agent (e.g. a particulate material, e.g. a particulate agent, e.g. a therapeutic agent, e.g. a particulate therapeutic agent), the dispenser including a longitudinally extending body comprising: a longitudinally extending base element; and an outer wrapper engaged around the base element; wherein a part of the outer wrapper extends longitudinally beyond a face of the base element to form a tubular element extending longitudinally from the base element, the inner wall of the tubular element defining a cavity; and optionally, an agent (e.g. a particulate material, e.g. a particulate agent, e.g. a therapeutic agent, e.g. a particulate therapeutic agent) within the cavity; the dispenser optionally including closure means for the cavity.

In this example/aspect, the outer wrapper is preferably a stiff outer wrapper (so that the tubular element that is formed by the outer wrapper is robust enough to withstand the filling and capping procedure). The outer wrapper may be a paper of basis weight from about 80 to 120 gsm, or a paper of basis weight 30 to 80 gsm to which additive has been applied to make it stiff, or which has been processed or formulated to create a stiffer structure than conventional plug wrap papers. The outer wrapper may be ventilated (e.g. with perforations, as is well known in the art).

The outer wrapper may be opaque or transparent. A transparent wrapper will allow the user to see if there is any agent (or any doses of agent) left in the cavity or reservoir. If there is any agent left in a single dose dispenser, the user is then able to suck again on the dispenser to ensure the full dose/amount of agent is dispensed.

The dispenser may include a closure means (e.g. a cap).

The closure means may be in the form of a sealing tape or sealing disc which is applied to the top of the tubular element [after the agent (e.g. a particulate material, e.g. a particulate agent, e.g. a therapeutic agent, e.g. a particulate therapeutic agent) has been inserted into the cavity] to hold the agent (e.g. a particulate material, e.g. a particulate agent, e.g. a therapeutic agent, e.g. a particulate therapeutic agent) in place.

Preferably the closure means (e.g. cap) may be removed (for the dispensing of agent) and then replaced (after the dispensing of the agent).

In an example, the closure means is a cap comprising a cap wrapper engaged around a (generally cylindrical) capping element; wherein a part of the cap wrapper extends beyond a first face of the capping element such that the inner walls of the cap wrapper which extend beyond the capping element define (with the first face of the capping element) a (generally cylindrical) recess. The dispenser may be capped by inserting the end of the longitudinally extending (e.g. generally cylindrical) body (the end which is opposite to the base element) into the recess. The cap helps keep the dispenser contents in place and may protect the end of the longitudinally extending body. Preferably, the cap wrapper and the longitudinally extending (e.g. generally cylindrical) body are dimensioned so there is a snug interference fit between the inner face of the cap wrapper and the outer surface of the longitudinally extending body (e.g. so the cap is held in place, but can be readily removed when the contents of the dispenser are to be dispensed). For example, the inner diameter of the cap wrapper may be slightly greater than the outer diameter of the longitudinally extending body. The cap wrapper is preferably a stiff cap wrapper. The cap wrapper may be a paper of basis weight from about 80 to 120 gsm, or a paper of basis weight 30 to 80 gsm to which additive has been applied to make it stiff, or which has been processed or formulated to create a stiffer structure than conventional plug wrap papers.

The capping element may be formed from a bonded fibrous structure, from a folded film, paper or nonwoven material, or formed via an extrusion or moulding process. The capping element may, for example, be made of cellulose acetate, polypropylene, polyester, bicomponent fibre, paper or any other similar material.

In another example, the closure is a cap comprising a (generally cylindrical) capping element and a generally cylindrical plug element which extends from one face of the capping element. The outer diameter of the plug element is slightly less that the inner diameter of the tubular element such that the plug element may fit snugly within the tubular element. This type of cap could, for example, be made of plastic via an injection moulding process.

In another example, the closure means may be cap which includes a second reservoir to hold a further amount or dose of agent (e.g. a particulate material, e.g. a particulate agent, e.g. a therapeutic agent, e.g. a particulate therapeutic agent), which can be dropped into the tube to provide a second dose of agent after the original dose has been consumed.

In another example, the closure means may be a cap comprising a (generally cylindrical) capping element. The capping element may be formed from a bonded fibrous structure, from a folded film, paper or nonwoven material, or formed via an extrusion or moulding process. The capping element may be abutted to (the open end of) the tubular element and held in place by a common wrapper which is engaged around the base element, the tubular element, and the capping element. The common wrapper may include a line of weakness substantially in register with (e.g. in register with, or within 5 mm of, preferably within 2 or 3 mm of) the junction between the (abutted) tubular element and capping element.

The common wrapper includes a line of weakness substantially in register with the junction between the (abutted) tubular element and capping element, along which the wrapper is snapped or torn to release the capping element and reveal the agent (so it can be dispensed). The line of weakness may be in register with the junction between the (abutted) tubular element and capping element, or within 5 mm of, preferably within 3 mm of, the junction between the (abutted) tubular element and capping element. It is preferred that the line of weakness is located over the tubular element. This positioning means that the line of weakness (and the cut) will be below the edge of the (e.g. tubular) element of the dispenser which is e.g. inserted into the e.g. mouth of the user, reducing the risk of sharp edges at the end of the dispenser (and reducing the risk of injury to the user when the dispenser is inserted into e.g. the user's mouth, ear etc.).

The common wrapper may be cellophane or BOPP, but it is preferred that the common wrapper is paper. The line of weakness may be a line of perforations (e.g. holes) in the wrapper. Preferably the line of weakness is a line which has been cut into (but not through) the wrapper, or scored into the wrapper. The line of weakness (e.g. scoring or perforation) indicates to the consumer where the product should be snapped. Preferably the common wrapper is a paper of basis weight from about 40 to 120 gsm, preferably a paper of basis weight 50 to 90 gsm, for example 60 gsm or 80 gsm. The applicants have found that scoring works better when the common product wrapper is a thicker or heavier-weight paper (with the additional advantage that the heavier weight paper also provides a better 'quality' feel to the product). Introduction of the line of weakness (e.g. scoring/perforating) may be carried out either before (to the wrapper) or after the product is assembled (after the wrapper has been engaged around the dispensers) (i.e. in-line).

The outer wrapper may be coloured or pigmented (e.g. black, grey, blue, red, brown or green), and/or may be transparent or transparent in selected regions to enable the user to see the underlying product. The outer wrapper may be printed with a suitable ink (notably black, grey or blue).

In an example, the outer wrapper may be chosen to render the contents of the dispenser invisible (which may be desirable). In this example, the outer wrapper may be of opacity 95% or greater. The outer wrapper is preferably printed with a suitable ink (notably black, grey or blue), e.g. to increase the opacity and thereby disguise the cavity. Printing the paper has the advantage of improving appearance of the outer wrapper but without affecting the runnability of the paper during the manufacturing process. It is also possible to print the outer wrapper on both sides (and/or have the printed surface on the inside or outside of the finished dispenser). In an alternative, the outer wrapper may comprise a foil or other opaque material attached (e.g. laminated) to the paper.

In another example, the longitudinally extending (e.g. generally cylindrical) body includes a longitudinally extending (e.g. generally cylindrical) base element; a (e.g. generally cylindrical) tubular element which extends longitudinally from the base element; and a (e.g. generally cylindrical) upper element which extends longitudinally from the tubular element; such that the inner wall of the tubular element defines (e.g. with the base element and the tubular element) the cavity (or reservoir); and wherein the upper element includes one of more channels which extend longitudinally from the cavity (reservoir) through the upper element. An agent (e.g. a particulate material, e.g. a particulate agent, e.g. a therapeutic agent, e.g. a particulate therapeutic agent) is located with the cavity/reservoir.

There is provided a dispenser for an agent (e.g. a particulate material, e.g. a particulate agent, e.g. a therapeutic agent, e.g. a particulate therapeutic agent), the dispenser including a longitudinally extending body comprising: a longitudinally extending base element; a tubular element extending longitudinally from the base element such that the inner wall of the tubular element defines a cavity; an upper element which extends longitudinally from the tubular element; wherein the upper element includes one or more channels which extend longitudinally from the cavity through the upper element, and optionally an agent (e.g. a particulate material, e.g. a particulate agent, e.g. a therapeutic agent, e.g. a particulate therapeutic agent) within the cavity;

the dispenser optionally including closure means. Preferably, the tubular element includes ventilation means (e.g. radial perforations) to allow ventilation air into the chamber. The tubular element may be formed by an outer wrapper (e.g. stiff paper wrapper) which is engaged around both the base element and the upper element (which is spaced longitudinally from the base element) such that the inner wall of the outer wrapper defines the cavity (reservoir) between the longitudinally spaced base element and the upper element.

In this example/aspect, the agent (e.g. a particulate material, e.g. a particulate agent, e.g. a therapeutic agent, e.g. a particulate therapeutic agent) is held in a cavity between two (e.g. fibrous, or other material) end segments. The upper element has a number of narrow channels defined therein, e.g. in a manner similar to that described in EP 1072201, through which the agent may be dispensed (e.g. sucked). Peripheral small air inlet holes may be provided around the outer circumference of the cavity, in a manner analogous to the ventilation of cigarette filters. This construction reduces the need for a closure means such as a cap, although an end cap may be used—e.g. as described in FIG. 1.

In another example, the longitudinally extending (e.g. generally cylindrical) body includes a longitudinally extending (e.g. generally cylindrical) base element;

a (e.g. generally cylindrical) tubular element which extends longitudinally from the base element, the inner wall of the tubular element defining (e.g. with the base element) a first cavity (or reservoir);

a (e.g. generally cylindrical) capping element which is distanced longitudinally from the end of the tubular element (e.g. the end of the tubular element which is opposite to the base element); and a common outer wrapper which is engaged around the base element, the tubular element and the capping element, the inner wall of the common outer wrapper defining a second cavity (or reservoir) between the tubular element and the capping element.

The common wrapper may include a line of weakness substantially in register with (e.g. in register with, or within 5 mm of, preferably within 2 or 3 mm of) the junction between the (abutted) tubular element and the base element.

An agent (e.g. a particulate material, e.g. a particulate agent, e.g. a foodstuff, e.g. a therapeutic agent, e.g. a particulate therapeutic agent) may be located within the first cavity/reservoir and/or the second cavity/reservoir.

There is provided a dispenser for an agent (e.g. a particulate agent, e.g. a foodstuff, e.g. a therapeutic agent, e.g. a particulate therapeutic agent), the dispenser including a longitudinally extending body comprising:

a longitudinally extending (e.g. generally cylindrical) base element;

a (e.g. generally cylindrical) tubular element which extends longitudinally from the base element, the inner wall of the tubular element defining (e.g. with the base element) a first cavity (or reservoir);

a (e.g. generally cylindrical) capping element which is distanced longitudinally from the end of the tubular element (e.g. the end of the tubular element which is opposite to the base element);

a common outer wrapper which is engaged around the base element, the tubular element and the capping element, the inner wall of the common outer wrapper defining a second cavity (or reservoir) between the tubular element and the capping element; and, optionally, an agent (e.g. a particulate material, e.g. a particulate agent, e.g. a foodstuff, e.g. a therapeutic agent, e.g. a particulate therapeutic agent) within the first and/or second cavity.

The common wrapper may include a line of weakness substantially in register with (e.g. in register with, or within 5 mm of, preferably within 2 or 3 mm of, for example 2 mm from) the junction between the (abutted) tubular element and the base element.

The common wrapper may include a line of weakness substantially in register with the junction between the (abutted) tubular element and the base element, along which the wrapper is snapped or torn to release the base element from the tubular element and reveal the first cavity (and agent therein, if present) so the agent can be dispensed. The line of weakness may be in register with the junction between the (abutted) tubular element and the base element, or within 5 mm of, preferably within 3 mm of, for example 2 mm from, the junction between the (abutted) tubular element and the base element. It is preferred that the line of weakness is located over the tubular element. This positioning means that the line of weakness (and the cut) will be below the edge of the (e.g. tubular) element of the dispenser which is e.g. inserted into the e.g. mouth of the user, reducing the risk of sharp (paper) edges at the end of the dispenser (and reducing the risk of injury to the user when the dispenser is inserted into e.g. the user's mouth, ear etc.).

The common wrapper may be cellophane or BOPP, but it is preferred that the common wrapper is paper. The line of weakness may be a line of perforations (e.g. holes) in the wrapper. Preferably the line of weakness is a line which has been cut into (but not through) the wrapper, or scored into the wrapper. The line of weakness (e.g. scoring or perforation) indicates to the consumer where the product should be snapped. Preferably the common wrapper is a paper of basis weight from about 40 to 120 gsm, preferably a paper of basis weight 50 to 90 gsm, for example 60 gsm or 80 gsm. The applicants have found that scoring works better when the common product wrapper is a thicker or heavier-weight paper (with the additional advantage that the heavier weight paper also provides a better 'quality' feel to the product). Introduction of the line of weakness (e.g. scoring/perforating) may be carried out either before (to the wrapper) or after the product is assembled (after the wrapper has been engaged around the dispensers) (i.e. in-line).

The outer wrapper may be coloured or pigmented (e.g. black, grey, blue, red, brown or green), and/or may be transparent or transparent in selected regions to enable the user to see the underlying product. The outer wrapper may be printed with a suitable ink (notably black, grey or blue).

The applicants have found that in examples with a first and second cavity, an agent in the second cavity may be visible, which is not always desirable. In examples, the outer wrapper may be chosen to render the contents of the dispenser invisible (which may be desirable). For example, the outer wrapper may be of opacity 95% or greater. The outer wrapper is preferably printed with a suitable ink (notably black, grey or blue), e.g. to increase the opacity and thereby disguise the cavity. Printing the paper has the advantage of improving appearance of the outer wrapper but without affecting the runnability of the paper during the manufacturing process. It is also possible to print the outer wrapper on both sides (and/or have the printed surface on the inside or outside of the finished dispenser). In an alternative, the outer wrapper may comprise a foil or other opaque material attached (e.g. laminated) to the paper.

The base element, tubular element and capping element may be formed from a bonded fibrous structure, from a folded film, paper or nonwoven material, or formed via an extrusion or moulding process. The base element and/or tubular element may, for example, be made of cellulose acetate, polypropylene, polyester, bicomponent fibre, paper or any other similar material. The base element is preferably porous. In this example, the capping element is preferably formed of a material which has a low pressure drop, for example a pressure drop of 5 to 350 mm water (for a 10 mm length×8 mm diameter element), for example a pressure drop of 5 to 250 mm water (for a 10 mm length×8 mm diameter element), more preferably a pressure drop of 10 to 300 mm water (for a 10 mm length×8 mm diameter element), for example a pressure drop of 10 to 200 mm water (for a 10 mm length×8 mm diameter element). The use of a porous material having a low pressure drop may facilitate ease of administration of the agent, e.g. by facilitating suction of the agent by the user.

The applicants have found that the inclusion of a first and second cavity facilitates manufacture and filling of the dispensers in a single pass process without requirement for the dispensers to be upright while being filled (see below). Further, the inclusion of a first and second cavity allows increased loading of agent (particulate material).

According to the invention, there is provided a method of production of dispensers for agents, the method comprising the steps of:

continuously advancing, longitudinally, a flow of (e.g. individual e.g. pre-formed) longitudinally extending (e.g. substantially cylindrical) rods which are arranged on a longitudinally advancing wrapper substrate between (e.g. pre-formed) longitudinally extending tubular elements, wherein each longitudinally extending (e.g. substantially cylindrical) rod in the advancing flow is arranged with a first end abutted to a first longitudinally extending tubular element, and a second end (e.g. the end opposite to the first end) adjacent to a space (gap) in the advancing flow between the second end of the longitudinally extending (e.g. substantially cylindrical) rod and a second longitudinally extending tubular element in the flow;

introducing an agent (e.g. a particulate material, e.g. particulate agent) into each space (gap) between a longitudinally extending (e.g. substantially cylindrical) rod and a longitudinally extending tubular element in the flow;

engaging (and e.g. fixing) the wrapper substrate around the longitudinally advancing flow to thereby form a continuous wrapped product rod comprising a plurality of longitudinally extending (e.g. substantially cylindrical) rods each arranged with a first end abutted to a first longitudinally extending tubular element, and a second end (e.g. the end opposite to the first end) adjacent to an additive containing cavity between the second end of the longitudinally extending (e.g. substantially cylindrical) rod and a second longitudinally extending tubular element.

According to the invention, the agent (e.g. a particulate material, e.g. particulate agent) may be snuff. The use of nasal snuff has been known for centuries. Snuff comes in the form of a finely ground, flavoured tobacco and is generally taken by a simple sniff into the nostrils. It is well-known that snuff interactions normally take place in the nasal mucus membranes of the user. Optionally, the method may include a further step of cutting the continuous wrapped product rod in register with each longitudinally extending (e.g. substantially cylindrical) rod, to thereby form (individual) dispensers for agents. It will be appreciated that each dispenser so formed includes a longitudinally extending body comprising: a longitudinally extending (e.g. generally cylindrical) base element; a (e.g. generally cylindrical) tubular element which extends longitudinally from the base element, the inner wall of the tubular element defining (e.g. with the base element) a first cavity (or reservoir); a (e.g. generally cylindrical) capping element which is distanced longitudinally from the end of the tubular element (e.g. the end of the tubular element which is opposite to the base element); a common outer wrapper which is engaged around the base element, the tubular element and the capping element, the inner wall of the common outer wrapper defining a second cavity (or reservoir) between the tubular element and the capping element; and an agent (e.g. a particulate material, e.g. a particulate agent, e.g. a foodstuff, e.g. a therapeutic agent, e.g. a particulate therapeutic agent) within at least the second cavity.

The applicants have found that the method according to this aspect of the invention allows manufacture and filling of dispensers in a single pass process without requirement for the dispensers to be upright prior to filling and capping.

In an example, the step of introducing an agent (e.g. a particulate material, e.g. particulate agent) into each space (gap) between a longitudinally extending (e.g. substantially cylindrical) rod and a longitudinally extending tubular element in the flow is performed while suction (e.g. a vacuum) is applied to the longitudinally extending tubular element which is adjacent to the space. If this is the case it is preferred that the longitudinally extending tubular elements are porous. In this example, the suction (vacuum) draws the agent (e.g. a particulate material, e.g. particulate agent) into the tubular element as the agent is introduced into the space (gap). This example allows increased additive loading because additive is located in a first cavity (within the tubular element) and the (second) cavity [which is between the second end of the longitudinally extending (e.g. substantially cylindrical) rod and the second longitudinally extending tubular element].

In another example, the step of introducing an agent (e.g. a particulate material, e.g. particulate agent) into each space (gap) between a longitudinally extending (e.g. substantially cylindrical) rod and a longitudinally extending tubular element in the flow is performed in the absence of suction or performed while suction (e.g. a vacuum) is applied to the longitudinally extending (e.g. substantially cylindrical) rod which is adjacent to the space. If this is the case it is preferred that the longitudinally extending (e.g. substantially cylindrical) rod is porous. In this example, little or no agent (e.g. a particulate material, e.g. particulate agent) is drawn into the tubular element as the agent is introduced into the space (gap) [e.g. because the vacuum sucks the agent towards the rod and retains the additive within the cavity]. This example limits the additive loading. The method may include a further step of introducing a line of weakness into the wrapper substantially in register with, or within 5 mm of, the or each junction between abutted tubular elements and rods in the advancing flow. This may be done by methods well known in the art, and referred to herein.

In another example, the longitudinally extending (e.g. generally cylindrical) body includes a longitudinally extending (e.g. generally cylindrical) base element; and a (e.g. generally cylindrical) tubular element which extends longitudinally from the base element, the tubular element comprising a (e.g. stiff) outer (tubular) wrapper engaged around a core element having a profiled (e.g. grooved e.g. corrugated) outer surface, the profiled outer surface of the core element defining with the (inner surface of the) outer (tubular) wrapper at least one (e.g. longitudinally extending) cavity.

There is provided a dispenser for an agent (e.g. a particulate material, e.g. a particulate agent, e.g. a therapeutic agent, e.g. a particulate therapeutic agent), the dispenser including a longitudinally extending body comprising: a longitudinally extending base element and a tubular element which extends longitudinally from the base element; the tubular element comprising an outer wrapper engaged around a core element having a profiled outer surface, the profiled outer surface of the core element defining with the outer wrapper at least one cavity; and optionally an agent (e.g. a particulate material, e.g. a particulate agent, e.g. a therapeutic agent, e.g. a particulate therapeutic agent) within the cavity; the dispenser optionally including closure means for the cavity.

Preferably the profiled outer surface of the core element defines with the (inner surface of the) outer (tubular) wrapper 4 to 16 (e.g. longitudinally extending) cavities. Preferably the (or each) cavity extends (e.g. continuously) the (full) length of the core element. The agent (e.g. a particulate material, e.g. a particulate agent, e.g. a therapeutic agent, e.g. a particulate therapeutic agent) is contained in the (or each) cavity. The outer (tubular) wrapper may comprise (or be) formed by a common wrapper which is engaged around both the base element and the core element.

It will be appreciated that in this example/aspect the agent (e.g. a particulate material, e.g. a particulate agent, e.g. a therapeutic agent, e.g. a particulate therapeutic agent) is held in an arrangement of one or more cavities around the outer circumference of the tubular element (rather than in a central tube).

The profiled (e.g. grooved or corrugated) surface of the core element may be formed in the surface of the core element (e.g. by thermoforming a fibrous material such as cellulose acetate), or may be formed by a profiled (e.g. corrugated e.g. paper) wrapper engaged around the core element.

The base element and the core element may be formed separately, or they may be of unitary construction. If the base element and core element are formed separately, the core element may be of similar construction to a Filtrona CPA filter (see WO2007/135414) having full length grooves. If the base element and core element are of unitary construction they may, for example, be formed as continuous common (e.g. fibrous) body which may, for example, be of similar construction to a CPA filter with a 'fluted' region uppermost and a 'bar' region lowermost.

In the above examples the base element and/or tubular element and/or upper element (where present) and/or core element (where present) may be formed from a bonded fibrous structure (e.g. cellulosed acetate), from a folded film, paper or nonwoven material, or formed via an extrusion or moulding process. The base element and/or tubular element and/or upper element (where present) and/or core element (where present) may, for example, be made of cellulose acetate, polypropylene, polyester, bicomponent fibre, paper or any other similar material. The longitudinally extending (e.g. generally cylindrical) body may further comprise a common wrapper which is engaged around the base element and/or the tubular element and/or the upper element (where present) and/or the core element (where present).

The total length of the dispenser (longitudinally extending body) may be from 20 to 120 mm. The base element, tubular element and upper element (if present) may each be of length 10 to 100 mm.

There is provided a dispenser for an agent (e.g. a particulate material, e.g. a particulate agent, e.g. a therapeutic agent, e.g. a particulate therapeutic agent), including a longitudinally extending (generally cylindrical) body comprising a longitudinally corrugated and/or at least partially fibrillated sheet, film or foil of zero or low smoke permeability material which has been gathered laterally into (e.g. cylindrical) rod form; and an agent (e.g. a particulate material, e.g. a particulate agent, e.g. a therapeutic agent, e.g. a particulate therapeutic agent), held within the rod. The agent (e.g. a particulate material, e.g. a particulate agent, e.g. a therapeutic agent, e.g. a particulate therapeutic agent), is held loosely within the folds of the film and can be dispensed (e.g. sucked) from the end of the rod. The dispenser may further comprise an outer wrapper which is engaged around the longitudinally extending (e.g. generally cylindrical) body. This kind of filter may be made by the methods disclosed in GB2118423.

The dispenser may include a flavouring agent (e.g. menthol, spearmint, cloves). The flavouring agent may be included in the base element and/or the tubular element and/or the upper element and/or the core element and/or the closure means (e.g. capping element). The flavouring agent may be added to the body (or cap) to provide a flavouring sensation, for example to disguise the taste of the (e.g. therapeutic) agent. These flavours can be added by techniques known in the cigarette filter manufacturing industry, for example through direct injection of liquid flavouring agent into the base element and/or tubular element and/or capping element, or through entrainment of a flavoured thread or tape (e.g. in the base element). In a further example, one or more of the base element and/or capping element and/or upper element and/or core element may include a breakable capsule containing a flavouring agent. The user may rupture the capsule shortly before use to help transfer additional flavours to the agent.

It will be appreciated that the base element and/or tubular element and/or the upper element and/or the core element and/or capping element may be made (and wrapped) in the same well known ways as filter elements/plugs are made for use in tobacco smoke filters. For example, the base element may be made in the same way as (and dimensioned similarly to) a conventional Non Wrapped Acetate filter. Thus, the dispensers have the advantage that they can be easily manufactured using technologies known in the cigarette filter manufacturing industry. It is also possible to add the agent (e.g. a particulate material, e.g. a particulate agent, e.g. a therapeutic agent, e.g. a particulate therapeutic agent) to the device/dispenser at the same time it is being made rather than in a separate downstream process, through adaptation of known processes used to add granular and particulate material to cigarette filters.

The longitudinally extending body may include a (e.g. liquid or solid) humectant. The humectants may be held within the body (e.g. in the base element) e.g. to help keep the agent (e.g. a particulate material, e.g. a particulate agent, e.g. a therapeutic agent, e.g. a particulate therapeutic agent), dry, which may aid in subsequent dispensation of the agent.

There is provided a product comprising a plurality (e.g. 2, 4, 6) of (discrete, identical or substantially identical) dispensers (e.g. arranged end-to-end in a mirror image relationship); and a common wrapper engaged around the dispensers. The common wrapper may be e.g. perforated paper, scored paper, cellophane or BOPP. The dispensers may be removed from the product rod individually, for example in a manner similar to the known 'Pop-a-Tip' filters, or in a manner similar to filters described in PCT application No. PCT/EP2013/060732 (where a plurality of individual filters are surrounded by a perforated paper wrap and individual filters are released from the others by "snapping off" the filter along a line of perforations, or tearing along the line of perforations), dependent on the characteristics of the common wrapper. It will be appreciated that these dispensers and products may be packed in groups (e.g. 10 or 20 products as set out above may be packaged in a carton similar to a cigarette pack), or products and dispensers may be packed individually in blister packs. Thus, a product rod may provide a plurality (e.g. 2, 4 or 6) dispensers, each with e.g. a single dose of additive.

There is provided a product comprising a plurality (e.g. 2 to 10, e.g. 2, 4, 6) of (discrete, identical or substantially identical) dispensers disclosed herein arranged (e.g. abutted) end-to-end; and a common product wrapper engaged around the dispensers, wherein the common product wrapper includes a line of weakness substantially in register with (e.g. in register with, or within 5 mm of, preferably within 3 mm of) the or each junction between (abutted) dispensers. Preferably the dispensers are arranged such that adjacent dispensers are oriented in the same direction along the product (so the base element of a dispenser is not arranged next to (abutted to) the base element of an adjacent dispenser. Preferably at least one dispenser does not include a cap, such that at least one dispenser is capped by the base element of the adjacent dispenser (e.g. which is abutted thereto).

The dispensers may be removed from the product rod individually, for example in a manner similar to the known 'Pop-a-Tip' filters, or in a manner similar to filters described in PCT application No. PCT/EP2013/060732 (where a plurality of individual filters are surrounded by a perforated paper wrap and individual filters are released from the others by "snapping off" the filter along a line of perforations, or tearing along the line of perforations), by releasing individual dispensers from the others (from the product) by "snapping off" a dispenser along the line of weakness—e.g. along a line of perforations or a line of scoring—dependent on the characteristics of the common product wrapper.

The common product wrapper includes a line of weakness substantially in register with the or each junction between (abutted) dispensers, along which the wrapper is snapped or torn to release an individual dispenser. The line of weakness may be in register with the or each junction between (abutted) dispensers, or within 5 mm of, preferably within 3 mm of, the or each junction between (abutted) dispensers. It is preferred that the line of weakness is distanced (e.g. located 1 to 3 mm) from the junction between (abutted) dispensers such that the line of weakness is located over a portion of the (or each) dispenser which is not the base element. This positioning means that the line of weakness (and the cut) will be below the edge of the (e.g. tubular) element of the dispenser which is inserted into the e.g. mouth of the user, reducing the risk of sharp edges at the end of the dispenser (and reducing the risk of injury to the user when the dispenser is inserted into the mouth, ear etc.).

The common product wrapper may be cellophane or BOPP, but it is preferred that the common product wrapper is paper. The line of weakness may be a line of perforations (e.g. holes) in the wrapper. Preferably the line of weakness is a line which has been cut into (but not through) the wrapper, or scored into the wrapper. The line of weakness (e.g. scoring or perforation) indicates to the consumer where the product should be snapped. Preferably the common product wrapper is a paper of basis weight from about 40 to 120 gsm, preferably a paper of basis weight 50 to 70 gsm, for example 60 gsm. The applicants have found that scoring works better when the common product wrapper is a thicker or heavier-weight paper (with the additional advantage that the heavier weight paper also provides a better 'quality' feel to the product). Introduction of the line of weakness (e.g. scoring/perforating) may be carried out either before (to the wrapper) or after the product is assembled (after the wrapper has been engaged around the dispensers) (i.e. in-line). This type of product is easier to assemble at high speed using cigarette filter making machinery, which is a significant benefit.

As set out above, the plurality (e.g. 2 to 10, e.g. 2, 4, 6) of dispensers are preferably arranged such that adjacent dispensers are oriented in the same direction along the product. The plurality (e.g. 2 to 10, e.g. 2, 4, 6) of dispensers may be arranged end-to-end in a mirror image relationship [such that adjacent dispensers are oriented in opposite directions along the product], although this is not preferred. If the dispensers are arranged end-to-end in a mirror image relationship, the line of weakness (scoring, perforation) should be in register with the or each junction between (abutted) dispensers.

It will be appreciated that these dispensers and products may be packed in groups (e.g. 10 or 20 products as set out above may be packaged in a carton similar to a cigarette pack), or products and dispensers may be packed individually in blister packs.

According to the present invention in a further aspect there is provided a method of production of a product comprising a plurality of dispensers comprising the steps of:
(a) continuously advancing a flow of dispensers according to any aspect of the invention, wherein the dispensers are arranged end-to-end (e.g. wherein adjacent dispensers are oriented in the same direction in the advancing flow)
(b) wrapping a common product wrapper around the continuously advancing flow of dispensers; and
(c) introducing a line of weakness into the wrapper substantially in register with, or within 5 mm of, the or each junction between dispensers in the advancing flow. The line of weakness is distanced from the junction between dispensers such that the line of weakness is located over a portion of the (or each) dispenser which is not the base element. The line of weakness may be a line of perforations (e.g. holes) in the wrapper. Preferably the line of weakness is a line which has been cut into (but not through) the wrapper, or scored into the wrapper. The line of weakness (e.g. scoring or perforation) indicates to the consumer where the product should be snapped. Introduction of the line of weakness (e.g. scoring/perforating) may be carried out either before (to the wrapper) or after the product is assembled (after the wrapper has been engaged around the dispensers) (i.e. in-line). This type of product is easier to assemble at high speed using cigarette filter making machinery, which is a significant benefit.

The outer product wrapper may be coloured or pigmented (e.g. red, brown or green), and/or may be transparent or transparent in selected regions to enable the user to see the underlying product.

There is provided a product comprising two (discrete, identical or substantially identical) dispensers as disclosed herein joined together [for example arranged end-to-end (e.g. base element to base element)]. The product may include a common wrapper engaged around the dispensers. Such a product may simultaneously provide two separate sources of agent, by being bent or snapped or separated (e.g. in the middle). Alternatively, a 'two-ended' dispenser fitted with capping means on each end may be provided, such that the user sucks or otherwise dispenses agent from one end and then later from the other end before discarding the device. This example may be used, for example, where the agent is to be dispensed into the user's ears, so there is one source of agent for each ear.

A dispenser for an agent (e.g. a particulate material, e.g. a particulate agent, e.g. a therapeutic agent, e.g. a particulate therapeutic agent) may consist of a longitudinally extending body consisting of: a longitudinally extending base element; a tubular element extending longitudinally from the base element such that the inner wall of the tubular element defines a cavity; and an agent (e.g. a particulate material, e.g. a particulate agent, e.g. a therapeutic agent, e.g. a particulate therapeutic agent), within the cavity; the dispenser optionally including closure means for the cavity.

Any dispenser or product disclosed herein may include a further coloured wrapper engaged therearound. This may be in addition to one or more other wrappers. The further coloured wrapper is coloured or pigmented (e.g. red, brown or green), and/or may be transparent or transparent in selected regions to enable the user to see the underlying product/dispenser.

The present invention will now be illustrated with reference to the following Examples and the attached drawings in which.

Figure 1:
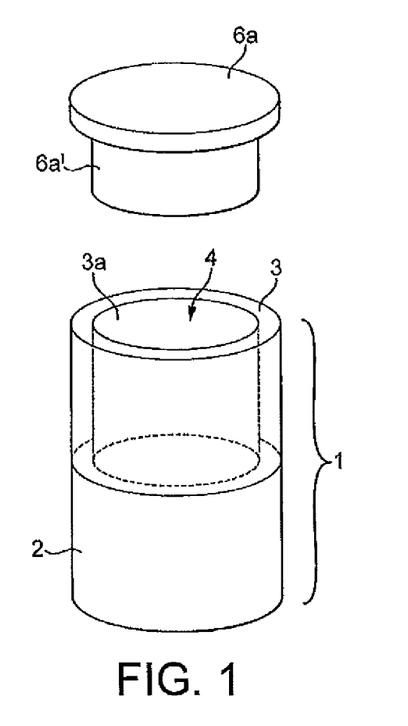
FIG. 1 schematically illustrates (not to scale) a dispenser.

FIG. 1 shows a dispenser. The dispenser has a longitudinally extending cylindrical body 1 which includes a longitudinally extending cylindrical base element 2 of length 20 mm and external diameter about 8 mm. The base element 2 is made of cellulose acetate and is porous (and of a low pressure drop of around 60 mm water) to facilitate ease of suction of the dispenser contents from the dispenser. A cylindrical tubular element 3 is abutted to the base element 2 and extends longitudinally from the base element 2. The tubular element 3 is made of cellulose acetate plasticised with triacetin, as is well-known from cigarette filter manufacture, and is of length 20 mm and external diameter about 8 mm. The inner wall 3a of the tubular element 3 defines, with the upper face of the base element 2, a cavity (reservoir) shown by arrow 4. The cavity 4 is of internal diameter 6 mm and depth 20 mm. The cavity includes a single dose of about 0.15 cm$^3$ of a particulate therapeutic agent (particulate material) in the form of powder (not shown). Examples of pharmaceuticals which are particulate materials (e.g. powders) for oral administration include Gaviscon Instants Oral Powder, marketed by Reckitt Benckiser Healthcare. It will be appreciated that this or other pharmaceutical for oral administration as a powder may be used with dispensers described herein (including the dispensers shown in FIGS. 1 to 4A).

The longitudinally extending cylindrical body 1 also includes a common wrapper (not shown) of paper plugwrap, which is engaged around the base element 2 and tubular element 3 and held in place with a lapped and (adhesive) stuck seam. The outer wrapper holds base element 2 and tubular element 3 in place; this type of construction is well-known from cigarette filter manufacture.

FIG. 1 also shows closure means in the form of a cap. In FIG. 1 the cap has been removed from the tubular body 1. The cap comprises a cylindrical capping element 6a and a generally cylindrical plug element 6a' which extends from one face of the capping element 6. The capping element 6a and plug element 6a' are of length 5 mm in total and formed in one piece from plastic via an injection moulding process. As can be seen in FIG. 1, the outer diameter of the plug element 6a' is slightly less that the inner diameter of the tubular element 3 such that the plug element 6a' may fit snugly within the tubular element 3. The plug element 6a' may be inserted into the open end of tubular element 3 (i.e. the end of tubular element 3 opposite to the base element 2) to plug the cavity 4 to thereby help retain the agent contents in place, and protect the end of the body 1. The outer diameter of the plug element 6a' is slightly less that the inner diameter of the tubular element 3, so there is a snug interference fit between the outer face of the plug element 6a' and the inner wall of the tubular element 3a. This means that the cap is held in place, but can be readily removed when the agent is to be dispensed.

In use, the user removes the cap (if present) and places the open end of the tube in their mouth and sucks the agent into their mouth.

Figure 2:
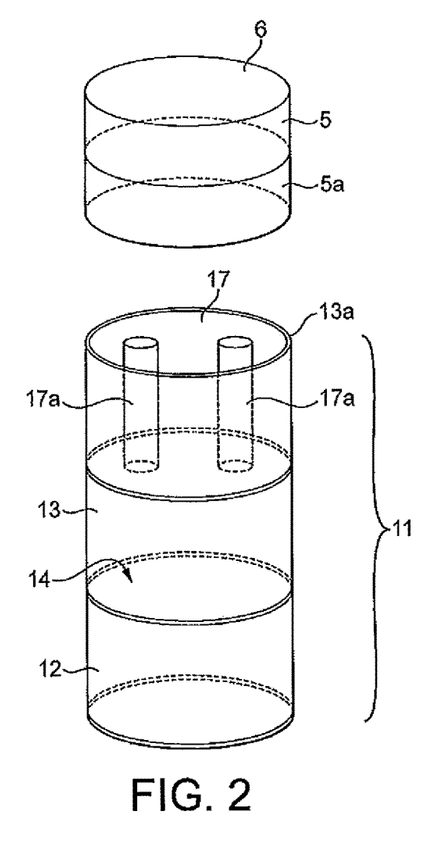
FIG. 2 schematically illustrates (not to scale) a different dispenser.

FIG. 2 shows a different example of a dispenser. The dispenser has a longitudinally extending cylindrical body 11 which includes a longitudinally extending cylindrical base element 12 of length 20 mm and external diameter about 8 mm. The base element 12 is made of cellulose acetate and is porous to facilitate ease of administration of the dispenser contents. The cylindrical body also includes a longitudinally extending cylindrical upper element 17 which is positioned at a distance of 10 mm from the base element 12 (that is, the distance between the top end of the base element and the bottom end of the upper element is 10 mm). Tubular element 13 is formed from an outer wrapper 13a of stiff paper of basis weight 80 gsm. The stiff paper is engaged around both the base element 12 and the upper element 17 (which is spaced longitudinally from the base element) to form tubular element 13 which extends between the base element 12 and the upper element 17. The inner walls of the stiff paper outer wrapper define a cavity (reservoir) 14 of diameter 8 mm and depth 10 mm extending between the longitudinally spaced base element 12 and upper element 17. The tubular element 13 (stiff paper 13a) is held in place around base element 12 and upper element 17 with a lapped and (adhesive) stuck seam. A particulate therapeutic agent (particulate material) in the form of powder (not shown) is located with the cavity/reservoir 14 (not shown). This type of construction is well-known from cigarette filter manufacture (it is somewhat similar to a triple granular filter), and it will be appreciated that construction of the dispenser (with the agent located in the cavity) will be readily achieved by methods known to those skilled in the art of cigarette manufacture.

The tubular element 13 includes ventilation means (peripheral small air inlet holes through the tubular element 13 around the outer circumference of cavity 14) in the stiff paper to allow ventilation air into the cavity 14. These are not shown, although it will be appreciated that these may be formed in a manner which is also analogous to the ventilation of cigarette filters.

The upper element 17 is a cylinder of outer diameter 8 mm and length 15 mm and is made of cellulose acetate. The upper element 17 includes two channels 17a, of diameter 2 mm, which extend longitudinally from the cavity (reservoir) 14 through the upper element 17. The upper element with the narrow channels defined therein may be made in a manner similar to that described in EP 1072201.

In this example, the therapeutic agent (particulate material) is held in cavity 14 between the base element 12 and the upper element 17, and may be dispensed by the user sucking the agent through channels 17a. This construction reduces the need for an end cap, although an end cap may be used as follows.

FIG. 2 also shows closure means in the form of a cap. In FIG. 2 the cap has been removed from the tubular body 11. The cap comprises a cylindrical capping element 6 formed from cellulose acetate tow. The capping element is of length 5 mm and has an external diameter slightly larger than that of the longitudinally extending cylindrical body 11 (see below). A stiff outer wrapper 5 formed from plugwrap paper of basis weight 80 gsm is engaged around capping element 6. Part 5a of the wrapper 5 of plugwrap paper extends beyond one face of capping element 6, such that the inner walls of the wrapper 5/5a which extend beyond capping element 6 define (with that face of the capping element 6) a recess. The end of upper element 17 (i.e. the end of upper element 17 opposite to the base element 12) may be inserted into the recess to cap the channels 17a, to thereby help retain the contents in place, and protect the end of the body 11. The inner diameter of the recess (formed by the inner walls of wrapper 5/5a) is slightly greater than the outer diameter of upper element 17 and surrounding tubular element 13 (stiff paper 13a), so there is a snug interference fit between the cap and the longitudinally extending body 11. This means that the cap is held in place, but can be readily removed when the contents are to be dispensed.

In use, the user removes the cap (if present) and places the open end of the tube (upper element 17 and channels 17a) in their mouth and sucks the agent (particulate material) through channels 17a. After use, the end (cap) may be placed over upper element 17 to cover the dispenser channels 17a.

Figure 3:
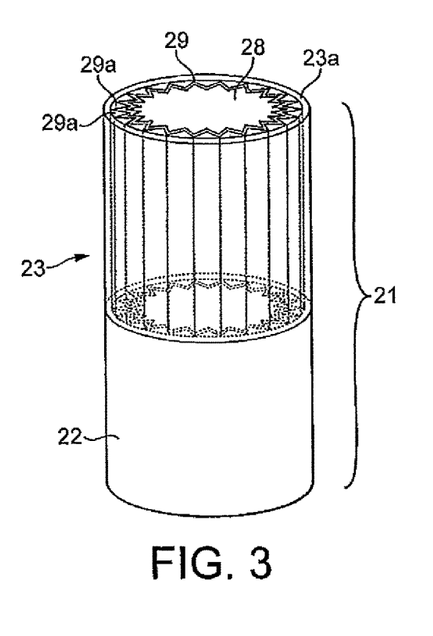
FIG. 3 schematically illustrates (not to scale) another different dispenser.

FIG. 3 shows another different example of a dispenser. The dispenser has a longitudinally extending cylindrical body 21 which includes a longitudinally extending cylindrical base element 22 of length 20 mm and external diameter about 8 mm. The base element 22 is made of cellulose acetate and is porous (and of a low pressure drop of around 60 mm water) to facilitate ease of dispensing of the agent. A cylindrical tubular element 23 extends longitudinally from the base element 22. The tubular element includes a core element 28 (extending longitudinally from the base element)

which has a corrugated outer surface. The core element 28 is made of cellulose acetate plasticised with triacetin and is surrounded by a corrugated paper wrapper 29. The core element is of length 20 mm and external diameter (at its broadest point) of about 8 mm. The longitudinally extending cylindrical body 21 also includes an outer wrapper 23a of paper plugwrap, which is engaged around the base element 22 and core element 28 and held in place with a lapped and (adhesive) stuck seam to hold base element 22 and corrugated core element 28 in place; this type of construction is well-known from cigarette filter manufacture. The corrugations in the outer surface of the corrugated paper wrapper 29 define, with the inner surface of the outer wrapper 23a, a number (14) of cavities 29a in the form of channels which extend longitudinally the full length of the core element/tubular element. In this construction, the tubular element 23 comprises the core element 28, the corrugated paper wrapper 29, the cavities 29a, and that portion of the outer wrapper 23a which is engaged around the core element 28. The illustrated tubular element/core element is of similar construction to a Filtrona CPA filter (see WO2007/135414).

The cavities 29a include therapeutic agent; together all cavities 29a include a single dose of about 0.15 cm$^3$ of the therapeutic agent in the form of a powder (not shown). In other words, the dose of agent (particulate material) is held in an arrangement of cavities 29a around the outer circumference of the tubular element (rather than in a central tubular cavity). An end cap may be used—e.g. as described with reference to FIG. 2.

Figure 4:
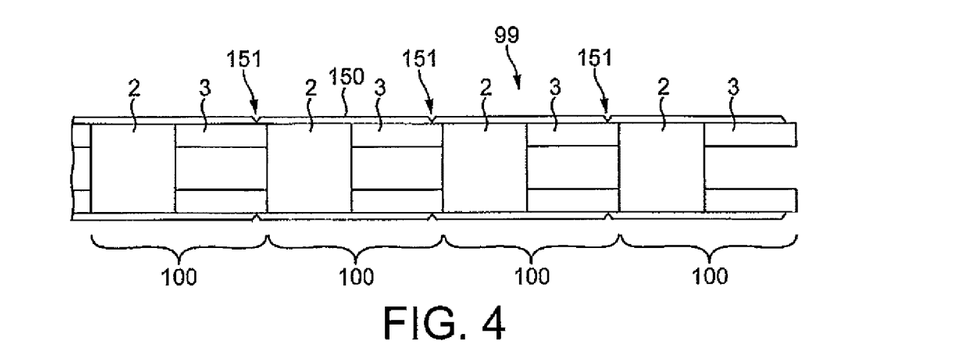
FIGS. 4 and 4A illustrate (not to scale) products which includes a plurality of dispensers similar to those illustrated in FIG. 1.

FIG. 4 illustrates (not to scale) a product 99 which includes a plurality of individual dispensers similar to those illustrated in FIG. 1. The product 99 of FIG. 4 comprises four identical dispensers 100 each of which include a longitudinally extending cylindrical body which includes a longitudinally extending cylindrical base element 2 of length 20 mm and external diameter about 8 mm; and a cylindrical tubular element 3 which is abutted to the base element 2 and extends longitudinally from the base element 2 such that the inner wall of the tubular element 3 defines, with the upper face of the base element 2, a cavity (reservoir) which includes a single dose of about 0.15 cm$^3$ of the same agent as described with reference to FIG. 1 above (not shown). The longitudinally extending cylindrical body also includes a common wrapper (not shown) of paper plugwrap, which is engaged around the base element 2 and tubular element 3 and held in place with a lapped and (adhesive) stuck seam. The outer wrapper holds base element 2 and tubular element 3 in place. The individual dispensers do not include caps.

The four dispensers 100 are arranged (e.g. abutted) end-to-end and, as seen in FIG. 4, the dispensers 100 are oriented in the same direction along the product (so the base element of a dispenser is not arranged next to (abutted to) the base element of an adjacent dispenser). A common product wrapper 150, in the form of a paper of basis weight 60 gsm, is engaged around the dispensers 100, and held in place with a lapped and (adhesive) stuck seam. The common product wrapper includes lines of weakness (shown by arrows 151) which are substantially in register with each junction between (abutted) dispensers.

The dispensers 100 may be removed from the others (i.e. from the product 99) by "snapping off" a dispenser along a line of weakness 151. The lines of weakness 151 are distanced 1 to 3 mm from the junction between (abutted) dispensers 100, such that the lines of weakness 151 are located over element 3 of the (or each) dispenser (which is not the base element). This positioning means that the line of weakness 151 (and the cut or snap) will be below the edge of the (e.g. tubular) element 3 of the dispenser which is inserted into the mouth of the user, reducing the risk of sharp edges at the end of the dispenser (and reducing the risk of injury to the user when the dispenser is inserted into the mouth).

The line of weakness 151 is a line which has been cut into (but not through) the wrapper, by scoring the wrapper (although it will be appreciated that the line of weakness may, in other examples, be a line of perforations). The line of weakness (e.g. scoring or perforation) indicates to the consumer where the product should be snapped. Introduction of the line of weakness (e.g. scoring/perforating) may be carried out either before (to the wrapper) or after the product is assembled (after the wrapper has been engaged around the dispensers) (i.e. in-line).

The product 99 may include a removable cap (e.g. similar to the cap shown in FIG. 1) for the dispenser at one end of the product which has an open tubular element 3. The cap is not shown.

Figure 4A:
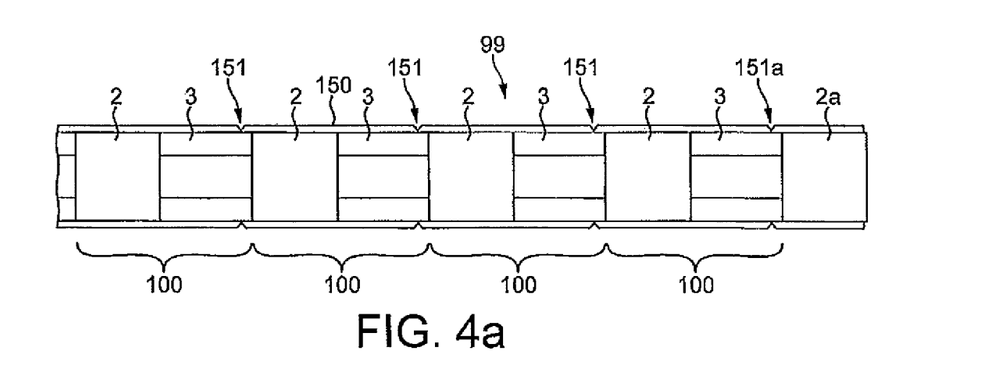

In another example, as shown in FIG. 4a, the cap may be an additional cellulose acetate cylindrical element 2a of length 20 mm and external diameter about 8 mm. The element 2a may be removed by e.g. snapping along adjacent line of weakness 151a. All other elements in FIG. 4a are identical to FIG. 4.

Figure 5:
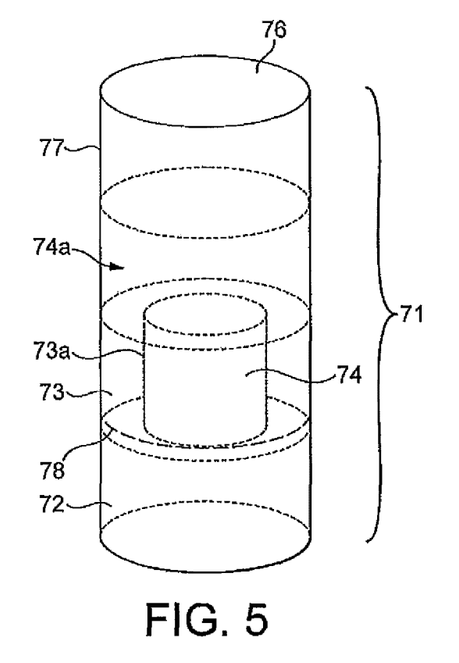
FIG. 5 schematically illustrates (not to scale) a further example of a dispenser.

FIG. 5 shows another example of a dispenser. The dispenser has a longitudinally extending cylindrical body 71 of length 82 mm and circumference 24.3 mm which includes a longitudinally extending cylindrical base element 72 of length 26 mm and external diameter about 7.6 mm. The base element 72 is made of cellulose acetate and is porous (and of a pressure drop of around 120 mm water). A cylindrical tubular element 73 extends longitudinally from the base element 72. The cylindrical tubular element 73 is abutted to the base element 72 and extends longitudinally from the base element 72. The tubular element 73 is made of cellulose acetate plasticised with triacetin, as is well-known from cigarette filter manufacture, and is of length 12 mm and external diameter about 7.6 mm. The inner wall 73a of the tubular element 73 defines, with the upper face of the base element 72, a first cavity (reservoir) within the tubular element shown by numeral 74. The first cavity 74 is of internal diameter about 4 mm and depth 12 mm. The first cavity includes a single dose of about 0.15 cm$^3$ of a particulate (e.g. therapeutic) agent (particulate material) in the form of powder (not shown), or may include a single shot of about 0.15 cm$^3$ of a particulate material such as a particulate foodstuff (e.g. sherbet), not shown. In another example, the first cavity includes a single dose of about 0.15 cm$^3$ of a particulate material in the form of snuff. The dispenser also includes a longitudinally extending capping element 76 of length 40 mm and external diameter about 7.6 mm. The capping element 76 is made of cellulose acetate and is porous (and of a pressure drop of around 180 mm water) to facilitate ease of dispensing of the agent (particulate material). The capping element 76 is distanced longitudinally from the end of the tubular element 73 (i.e. distanced longitudinally from the end of tubular element which is opposite to the base element), so there is a distance of 4 mm between the capping element 76 and the tubular element 73. The longitudinally extending cylindrical body 71 also includes a common outer wrapper 77 of paper plugwrap of basis weight 80 gsm, which is engaged around the base element 72, tubular element 73 and capping element 76 and held in place with a lapped and (adhesive) stuck seam to hold elements 72, 73 and 76 in place such that the inner wall of the common outer wrapper 77 defines a second cylindrical cavity (or reservoir) 74a, of diameter approximately 7.6 mm and depth 4 mm, between the tubular element and the capping element. The common wrapper includes a line of weakness 78 (shown by dashed line in FIG. 3) around the circumference of the longitudinally extending body 71 located around 2 mm from the junction between the (abutted) tubular element and the base element, along which the wrapper is snapped or torn to release the base element from the tubular element and reveal the first cavity so the agent can be dispensed. The line of weakness 78 is located over the tubular element. This positioning means that the line of weakness (and the cut) will be below the edge of the (e.g. tubular) element of the dispenser which is e.g. inserted into the e.g. mouth of the user, reducing the risk of sharp edges at the end of the dispenser (and reducing the risk of injury to the user when the dispenser is inserted into e.g. the user's mouth, ear etc.). The outer wrapper is printed with a suitable ink (notably black, grey or blue), e.g. to increase the opacity and thereby disguise the second cavity and additive therein. Printing the paper has the advantage of improving appearance of the outer wrapper but without affecting the runnability of the paper during the manufacturing process.

The user grasps the 26 mm long base element 72 and pulls or snaps it so that it breaks at the perforations, so the base element 72 can be removed to expose the end of the tubular element 73. It will be appreciated that the exposed end of the tubular element 73 is the end of the tubular element which is opposite the cavity 74a. The user may then discard the base element and hold the remainder of the dispenser to dispense the agent (particulate material) through the exposed end of the tubular element 73 (e.g. to the users mouth or nose, depending on the agent).

Figure 6:
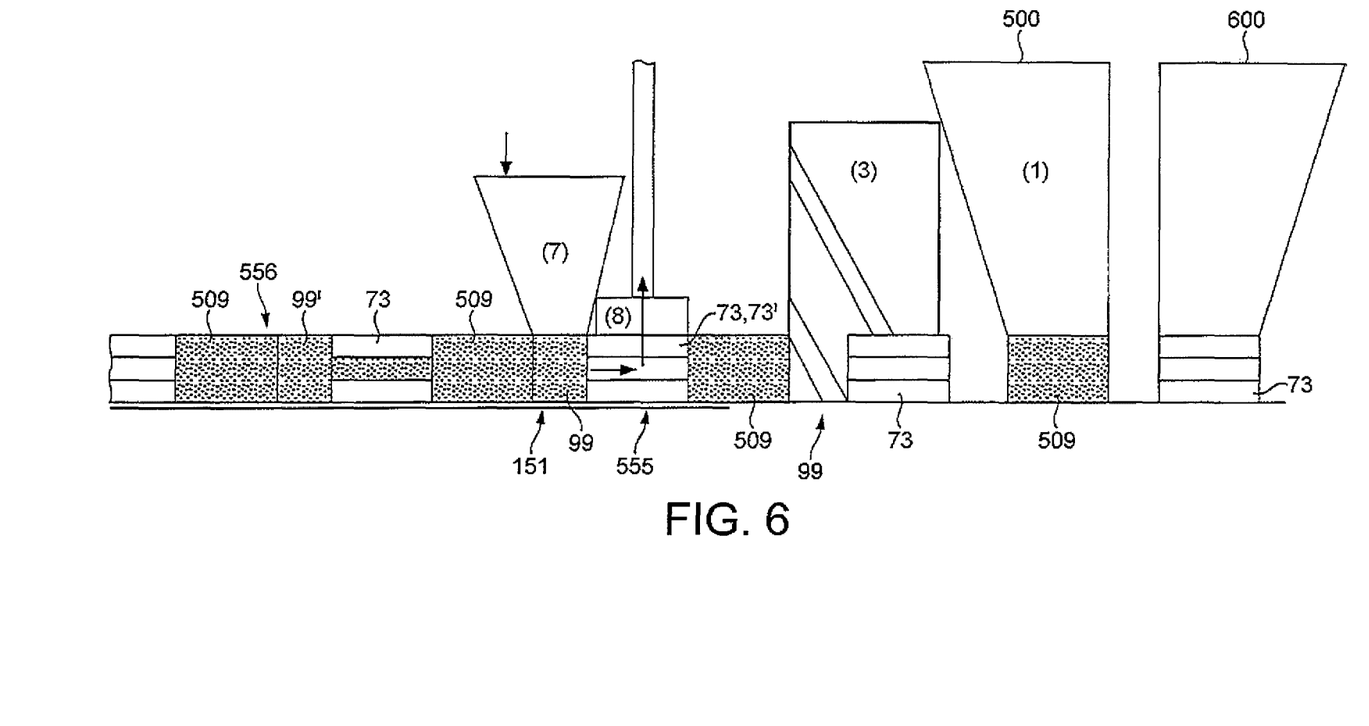
FIG. 6 illustrates apparatus for manufacturing the dispensers shown in FIG. 5 according to an example of a method according to the invention.

FIG. 6 shows an apparatus for making the dispensers of FIG. 5 in a continuous process according to the invention, which uses conventional cigarette filter making machinery.

As shown in FIG. 6 a first hopper 500 [also shown by (1)] releases individual pre-formed longitudinally extending substantially cylindrical rods 509, formed from cellulose acetate, and each of length 66 mm. A second hopper 600 releases pre-formed longitudinally extending tubular elements 73 cut to length 12 mm, which are formed of cellulose acetate plasticised with triacetin, and are porous. Hoppers 500 and 600 release rods 509 and tubular elements 73 respectively to form a continuously longitudinally advancing flow of alternating rods 509 and tubular elements 73 which advances in the direction of arrow 510.

The rods 509 and tubular elements 73 are picked up by a collator drum (3), with the collator drum "pushing" on rods 509 such that the rod is pushed such that each longitudinally extending (e.g. substantially cylindrical) rod 509 in the advancing flow is arranged with a first end abutted to a longitudinally extending tubular element 73, and its second end (the end opposite to the first end) adjacent to a space (gap) 99 in the advancing flow between the second end of the longitudinally extending (e.g. substantially cylindrical) rod 509 and a second longitudinally extending tubular element 73 in the flow. This process forms a continuously advancing, longitudinally, flow of (e.g. individual e.g. preformed) longitudinally extending (e.g. substantially cylindrical) rods 509 which are arranged between (e.g. preformed) longitudinally extending tubular elements 73, wherein each longitudinally extending (e.g. substantially cylindrical) rod 509 in the advancing flow is arranged with a first end abutted to a first longitudinally extending tubular element 73, and a second end (e.g. the end opposite to the first end) adjacent to a space (gap) 99 in the advancing flow between the second end of the longitudinally extending (e.g. substantially cylindrical) rod 509 and a second longitudinally extending tubular element 73 in the flow.

As shown in FIG. 6, the longitudinally advancing flow enters a garniture 555 where it becomes entrained on a longitudinally advancing wrapper substrate in the form of a paper of basis weight 80 gsm, which may be printed (e.g. with blue ink). As can be seen in FIG. 6, the flow is arranged on a longitudinally advancing wrapper substrate in the following order: rod 509+cavity 99+tubular element 73+rod 509 and so on.

The powdered agent (5) (e.g. particulate material, e.g. particulate agent) is introduced into each space (gap) 99 between a longitudinally extending (e.g. substantially cylindrical) rod 509 and a longitudinally extending tubular element 73 in the flow, using a Hamburg shoe (7), which drops the additive (particulate material) using gravity and/or use of a vibrating device (7) where required. This method is well known in the art of making tobacco smoke filters. Snuff may be used as the particulate agent (instead of e.g. a therapeutic agent, foodstuff such a sherbet etc.).

In the illustrated example, the step of introducing an agent (e.g. particulate agent, e.g. snuff) into each space (gap) 99 between a longitudinally extending (e.g. substantially cylindrical) rod 509 and a longitudinally extending tubular element 73 in the flow is performed while suction (e.g. a vacuum) is applied to the longitudinally extending tubular element 73' which is adjacent to the space 99, by suction means (8). In the illustrated example, the suction means is upstream of the Hamburg shoe. The suction means [inlet (8)] removes excess powdered additive (5), and at the same time creates a vacuum over the tubular element 73', which is porous. The suction (vacuum) draws the agent (e.g. particulate material, e.g. particulate agent) (5) into the hollow part of the tubular element 73' as the agent is introduced into the space (gap) 99. This example allows increased additive loading because additive is located in a first cavity (within the tubular element) and the (second) cavity 99 [which is between the second end of the longitudinally extending (e.g. substantially cylindrical) rod and the second longitudinally extending tubular element].

The garniture engages (and fixes) the wrapper substrate around the longitudinally advancing flow, by methods well known in the art of making tobacco smoke filters, to thereby form a continuous wrapped product rod 556 comprising a plurality of longitudinally extending (e.g. substantially cylindrical) rods 509 each arranged with a first end abutted to a first longitudinally extending tubular element 73, and a second end (e.g. the end opposite to the first end) adjacent to an additive containing cavity 99' between the second end of the longitudinally extending (e.g. substantially cylindrical) rod 509 and a second longitudinally extending tubular element 73.

The continuous wrapped product rod may then be cut (by a rotary knife or similar). The continuous wrapped rod may be cut in register with the (each) rod 509 (at a position 40 mm along each rod) such that the product rod is cut into individual dispensers as shown in FIG. 5. The continuous wrapped product rod is cut in register with each longitudinally extending (e.g. substantially cylindrical) rod 509, to thereby form (individual) dispensers 71 for agents. It will be appreciated that each dispenser 71 so formed includes a longitudinally extending body comprising: a longitudinally extending (e.g. generally cylindrical) base element 72; a (e.g. generally cylindrical) tubular element 73 which extends longitudinally from the base element, the inner wall of the tubular element defining (e.g. with the base element) a first cavity (or reservoir); a (e.g. generally cylindrical) capping element 76 which is distanced longitudinally from the end of the tubular element 73 (e.g. the end of the tubular element which is opposite to the base element); a common outer wrapper 77 which is engaged around the base element, the tubular element and the capping element, the inner wall of the common outer wrapper defining a second cavity (or reservoir) between the tubular element and the capping element; and an agent (e.g. particulate material, e.g. a particulate agent, e.g. a foodstuff, e.g. snuff, e.g. a therapeutic agent, e.g. a particulate therapeutic agent) within at least the second cavity. It will be appreciated that base element 72 and capping element 76 are formed the rod 509 by cutting the rod 509 into two.

It will be appreciated that in the above method the resulting rod may have both the cavity and the tubular element filled with the powdered particulate material (because of suction applied to the tubular element 73 while the cavity is being filled).

It will be appreciated that a line of weakness may be introduced into the wrapper substantially in register with, or within 5 mm of, the or each junction between abutted tubular elements 73 and rods 509 in the advancing flow, by methods well known in the art.

In another example, the step of introducing an agent (e.g. particulate material, e.g. particulate agent e.g. snuff) into each space (gap) between a longitudinally extending (e.g. substantially cylindrical) rod and a longitudinally extending tubular element in the flow is performed in the absence of suction or performed while suction (e.g. a vacuum) is applied to the longitudinally extending (e.g. substantially cylindrical) rod which is adjacent to the space. In this example, little or no agent (e.g. particulate material, e.g. particulate agent e.g. snuff) is drawn into the tubular element as the agent is introduced into the space (gap) [e.g. because the vacuum sucks the agent towards the rod and retains the additive within the cavity]. This example limits the additive loading. Thus, in order to avoid (or minimise) the filling of the tubular element with particulate material, with the illustrated apparatus, the feeding order of segments by the collator drum (3) would be changed (not shown) such that the order entering the garniture 555 is: rod 509+tubular element 73+cavity 99+rod 509, etc. This means that, for the apparatus, the tubular element would be downstream of the suction inlet as the cavity 99 is being filled, and the suction inlet is located over a rod 509. This means that when the cavity 99 is filled, powdered/particulate material does not enter the inside of the tubular element 73 (because it is being sucked upstream towards the rod 509 over which the suction means is placed). The position of the later cutting (along the rods 509) may also be adjusted, by methods known in the art, such that a mirror version of the product is obtained. Thus, the apparatus of FIG. 6 can be adapted so dispensers 71 may be formed, either with or without particulate material in the tubular element.

The hoppers, garniture, Hamburg shoe, suction device etc. are all well known in the tobacco smoke filter making art.

A key advantage of the FIG. 5 and FIG. 6 product/process in particular is that the dispensers may be made on standard tobacco smoke filter making equipment rather than requiring special processes where the tube section needs to be held in a vertical orientation to enable the tube section to be filled.

The invention claimed is:

1. A method of production of dispensers for agents, the method comprising the steps of:
   continuously advancing, longitudinally, a flow of longitudinally extending rods which are arranged on a longitudinally advancing wrapper substrate between longitudinally extending tubular elements, wherein each longitudinally extending rod in the advancing flow is arranged with a first end abutted to a first longitudinally extending tubular element, and a second end adjacent to a space in the advancing flow between the second end of the longitudinally extending rod and a second longitudinally extending tubular element in the flow;
   introducing an agent into each space between a longitudinally extending rod and a longitudinally extending tubular element in the flow;
   engaging the wrapper substrate around the longitudinally advancing flow to thereby form a continuous wrapped product rod comprising a plurality of longitudinally extending rods each arranged with a first end abutted to a first longitudinally extending tubular element, and a second end adjacent to an additive containing cavity between the second end of the longitudinally extending rod and a second longitudinally extending tubular element.

2. A method according to claim 1 including a further step of cutting the continuous wrapped product rod in register with each longitudinally extending rod, to thereby form dispensers for agents.

3. A method according to claim 1 in which the step of introducing an agent into each space between a longitudinally extending rod and a longitudinally extending tubular element in the flow is performed while suction is applied to the longitudinally extending tubular element which is adjacent to the space.

4. A method according to claim 1 in which the step of introducing an agent into each space between a longitudinally extending rod and a longitudinally extending tubular element in the flow is performed in the absence of suction or performed while suction is applied to the longitudinally extending rod which is adjacent to the space.

5. A method according to claim 1 including a further step of introducing a line of weakness into the wrapper substantially in register with, or within 5 mm of, the or each junction between abutted tubular elements and rods in the advancing flow.

6. A method according to claim 1 in which the agent is a particulate material.

7. A method according to claim 1 in which the agent is snuff.

8. A method according to claim 1, further including: dispensing the agent.

9. A method according to claim 1, wherein:
   the wrapper substrate is the only item engaged around the longitudinally advancing flow.

* * * * *